United States Patent [19]
Young

[11] Patent Number: 5,677,279
[45] Date of Patent: Oct. 14, 1997

[54] METHODS AND COMPOSITIONS FOR TREATING PAIN WITH AMYLIN OR AGONISTS THEREOF

[75] Inventor: Andrew A. Young, San Diego, Calif.

[73] Assignee: Amylin Pharmaceuticals, Inc., San Diego, Calif.

[21] Appl. No.: 767,169

[22] Filed: Dec. 16, 1996

[51] Int. Cl.$^6$ ............................................. A61K 38/22
[52] U.S. Cl. ............................................. 514/12
[58] Field of Search ............................................. 514/12

[56] References Cited

U.S. PATENT DOCUMENTS

| | | |
|---|---|---|
| 5,124,314 | 6/1992 | Cooper . |
| 5,175,145 | 12/1992 | Cooper . |
| 5,234,906 | 8/1993 | Young et al. . |
| 5,264,372 | 11/1993 | Beaumont et al. . |
| 5,266,561 | 11/1993 | Cooper et al. . |
| 5,367,052 | 11/1994 | Cooper et al. . |
| 5,376,638 | 12/1994 | Young et al. . |

OTHER PUBLICATIONS

Alam et al., *Biochem. Biophys. Res. Commun.*, 179(1):134–139 (1991).
Beaumont et al., *Br. J. Pharmacol.*, 115(5):713–715 (1995).
Berebaum, *J. Theor. Biol.* 144:413 (1985).
Bouali, *Regul. Peptides*, 56:167–174 (1995).
Brain et al., *Eur. J. Pharmacol.*, 183:2221 (1990).
Broderick et al., *Biochem. Biophys. Res. Commun.*, 177:932–938 (1991).
Brown et al., *Diabetes* 43(Suppl 1):172A (1994).
Chance et al., *Brain Res.*, 539:352–354 (1991).
Chantry et al., *Biochem. J.*, 277:139–143 (1991).
Cooper et al., *Biochem. Biophys. Acta*, 1014:247–258 (1989).
Cooper et al., *Prog. Growth Factor Research*, 1:99–105 (1989).
Cooper et al., *Proc. Natl. Acad. Sci.*, 85:7763–7766 (1988).
Cooper et al., *Proc. Natl. Acad. Sci. USA*, 84:8628–8632 (1987).
Deems et al., *Biochem. Biophys. Res. Commun.*, 181(1):116–120 (1991).
Follett et al., *Clinical Research*, 39(1):39A (1991).
Gaeta and Rink, *Med. Chem. Res.*, 3:483–490 (1994).
Galeazza et al., *Peptides*, 12:585–591 (1991).
Gardiner et al., *Diabetes*, 40:948–951 (1991).
Gedulin et al., *Diabetologia*, 38 (Suppl 1):A244 (1995).
Gedulin et al., *Biochem. Biophys. Res. Commun.*, 180(1):782–789 (1991).
Gill et al., *Life Sciences*, 48:703–710 (1991).
Gomez-Foix et al., *Biochem J.*, 276:607–610 (1991).
Hartter et al., *Diabetologia*, 34:52–54 (1991).
Hendershot and Forsaith, *J. Pharmacol. Expt. Therap.*, 125:237–240 (1959).
Huang et al., *Hypertension*, 19:I-101–I-109 (1991).
Kanatsuka et al., *FEBS Letts.*, 259(1), 199–201 (1989).
Koda et al., *The Lancet*, 339:1179–1180 (1992).
Koopmans et al., *Diabetologia*, 34:218–224 (1991).
Leighton and Cooper, *Nature*, 335:632–635 (1988).
Macdonald et al., *Diabetologia* 38 (Suppl 1):A32 (abstract 118) (1995).
Merskey, *Pain*, 6:249 (1979).
Molina et al., *Diabetes*, 39:260–265 (1990).
Moore et al., *Biochem. Biophys. Res. Commun.*, 179(1) (1991).
Munson and Rodbard, *Anal. Biochem.* 107:220–239 (1980).
Nowak et al., *J. Lab. Clin. Med.*, 123(1):110–6 (1994).
Ogawa et al., *J. Clin. Invest.*, 85:973–976 (1990).
Ohsawa et al., *Biochem. Biophys. Res. Commun.*, 160(2):961–967 (1989).
Pittner et al., *FEBS Letts.*, 365(1):98–100 (1995).
Pittner et al., *J. Cell. Biochem.*, 55S:19–28 (1994).
Plourde et al., *Life Sci.*, 53:857–862 (1993).
Rink et al., *Trends in Pharmaceutical Sciences*, 14:113–118 (1993).
Roden et al., *Diabetologia*, 35:116–120 (1992).
Sanke et al., *Diabetologia*, 34:129–132 (1991).
Scarpignato et al., *Arch. Int. Pharmacodyn. Ther.*, 246:286–295 (1980).
Silvestre et al., *Reg. Pept.*, 31:23–31 (1991).
Stephens et al., *Diabetes*, 40:395–400 (1991).
Wang et al., *FEBS Letts.*, 291:195–198 (1991).
Young et al., *Diabetologia* 38(6):642–648 (1995).
Young et al., *Mol. Cell. Endocrinol.*, 84:R1–R5 (1992).
Young et al. *Amer. J. Physiol.*, 259:45746–1 (1990).
Young et al., *FEBS Letts*, 281(1,2):149–151 (1991).
Young et al., *Am. J. Physiol.*, 263(2):E274–E281 (1992).
Zaidi et al., *Trends in Endocrinal. and Metab.*, 4:255–259 (1993).
Zhu et al., *Biochem. Biophys. Res. Commun.*, 177(2):771–776 (1991).
(*Introduction to Cleavage Techniques*, Applied Biosystems, Inc., 1990, pp. 6–12).
Cohen, et al., *The Pico Tag Method: A Manual of Advanced Techniques for Amino Acid Analysis*, pp. 11–52, Millipore Corporation, Milford, MA (1989).

*Primary Examiner*—William R.A. Jarvis
*Attorney, Agent, or Firm*—Lyon & Lyon

[57] ABSTRACT

Methods for treating pain are disclosed which comprise administration of a therapeutically effective amount of an amylin or an amylin agonist alone or in conjunction with a narcotic analgesic or other pain relief agent.

22 Claims, 10 Drawing Sheets

Mean ± SE % inhibition of the writhing response after s.c administration of saline (open squares) or rat-amylin, 3 µg/kg (closed squares) in animals treated with 0.01, 0.1 and 3 mg/kg doses of morphine (i.p); N ≥ 6

* = P < 0.05

Mean ± SE % inhibition of the writhing response after s.c administration of saline (open squares) or rat-amylin, 10 µg/kg (closed squares) in animals treated with 0.01, 0.1 and 3 mg/kg doses of morphine (i.p); N ≥ 8

* = P < 0.05

METHODS AND COMPOSITIONS FOR TREATING PAIN WITH AMYLIN OR AGONISTS THEREOF

FIELD OF THE INVENTION

The present invention relates to methods for treating pain. More particularly, the invention relates to the use of an amylin or agonist of amylin in the treatment of pain, either alone or in combination with a narcotic analgesic or other pain relief agent.

BACKGROUND

Amylin

The structure and biology of amylin have previously been reviewed. See, for example, Rink et al., *Trends in Pharmaceutical Sciences*, 14:113–118 (1993); Gaeta and Rink, *Med. Chem. Res.*, 3:483–490 (1994); and, Pitther et al., *J. Cell. Biochem.*, 55S:19–28 (1994). Amylin is a 37 amino acid protein hormone. It was isolated, purified and chemically characterized as the major component of amyloid deposits in the islets of pancreases of deceased human Type 2 diabetics (Cooper et al., *Proc. Natl. Acad. Sci. USA*, 84:8628–8632 (1987)). The amylin molecule has two important post-translational modifications: the C-terminus is amidated, and the cysteines in positions 2 and 7 are cross-linked to form an N-terminal loop. The sequence of the open reading frame of the human amylin gene shows the presence of the Lys-Arg dibasic amino acid proteolytic cleavage signal, prior to the N-terminal codon for Lys, and the Gly prior to the Lys-Arg proteolytic signal at the C-terminal position, a typical sequence for amidation by protein amidating enzyme, PAM (Cooper et al., *Biochem. Biophys. Acta*, 1014:247–258 (1989)). Amylin is the subject of U.S. Pat. No. 5,367,052, issued Nov. 22, 1995.

In Type 1 diabetes, amylin has been shown to be deficient and combined replacement with insulin has been proposed as a preferred treatment over insulin alone in all forms of diabetes. The use of amylin and other amylin agonists for the treatment of diabetes mellitus is the subject of U.S. Pat. No. 5,175,145, issued Dec. 29, 1992. Pharmaceutical compositions containing amylin and amylin plus insulin are described in U.S. Pat. No. 5,124,314, issued Jun. 23, 1992.

Excess amylin action has been said to mimic key features of Type 2 diabetes and amylin blockade has been proposed as a novel therapeutic strategy. It has been disclosed in U.S. Pat. No. 5,266,561, issued Nov. 30, 1993, that amylin causes reduction in both basal and insulin-stimulated incorporation of labeled glucose into glycogen in skeletal muscle. The latter effect was also disclosed to be shared by calcitonin gene related peptide (CGRP) (see also Leighton and Cooper, *Nature*, 335:632–635 (1988)). Amylin and CGRP were approximately equipotent, showing marked activity at 1 to 10 nM. Amylin is also reported to reduce insulin-stimulated uptake of glucose into skeletal muscle and reduce glycogen content (Young et al., *Amer. J. Physiol.*, 259:45746–1 (1990)). The treatment of Type 2 diabetes and insulin resistance with amylin antagonists is disclosed.

The chemical structure of amylin is nearly 50% identical to the CGRPs, also 37 amino acid proteins which are widespread neurotransmitters with many potent-biological actions, including vasodilation. Amylin and CGRP share the $^2$Cys-$^7$Cys disulphide bridge and the C-terminal amide, both of which are essential for full biologic activity (Cooper et al., *Proc. Natl. Acad. Sci. USA*, 857763–7766 (1988)). Amylin reportedly may be one member of a family of related peptides which includes CGRP, insulin, insulin-like growth factors and the relaxins and which share common genetic heritage (Cooper et al., *Prog. Growth Factor Research*, 1:99–105 (1989)).

Amylin is primarily synthesized in pancreatic beta cells and is secreted in response to nutrient stimuli such as glucose and arginine. Studies with cloned beta-cell tumor lines (Moore et al., *Biochem. Biophys. Res. Commun.*, 179(1) (1991)), isolated islets (Kanatsuka et al., *FEBS Letts.*, 259(1), 199–201 (1989)) and perfused rat pancreases (Ogawa et al., *J. Clin. Invest.*, 85:973–976 (1990)) have shown that short pulses, 10 to 20 minutes, of nutrient secretagogues such as glucose and arginine, stimulate release of amylin as well as insulin. The molar amylin:insulin ratio of the secreted proteins varies between preparations from about 0.01 to 0.4, but appears not to vary much with acute stimuli in any one preparation. However, during prolonged stimulation by elevated glucose, the amylin:insulin ratio can progressively increase (Gedulin et al., *Biochem. Biophys. Res. Commun.*, 180(1):782–789 (1991)). Thus, amylin and insulin are not always secreted in a constant ratio.

It has been discovered and reported that certain actions of amylin are similar to non-metabolic actions of CGRP and calcitonin; however, the metabolic actions of amylin discovered during investigations of this newly identified protein appear to reflect its primary biologic role. At least some of these metabolic actions are mimicked by CGRP, albeit at doses which are markedly vasodilatory (see, e.g., Leighton et al., *Nature*, 335:632–635 (1988)); Molina et al., *Diabetes*, 39:260–265 (1990)).

The first discovered action of amylin was the reduction of insulin-stimulated incorporation of glucose into glycogen in rat skeletal muscle (Leighton et al., *Nature*, 335:632–635 (1988)); the muscle was made "insulin-resistant." Subsequent work with rat soleus muscle ex-vivo and in vitro has indicated that amylin reduces glycogen synthase activity, promotes conversion of glycogen phosphorylase from the inactive b form to the active a form, promotes net loss of glycogen (in the presence or absence of insulin), increases glucose-6-phosphate levels, and can increase lactate output (see, e.g., Deems et al., *Biochem. Biophys. Res. Commun.*, 181(1):116–120 (1991)); Young et al., *FEBS Letts*, 281(1, 2):149–151 (1991)). Amylin appears not to affect glucose transport per se (e.g., Pittner et al., *FEBS Letts.*, 365(1):98–100 (1995)). Studies of amylin and insulin dose-response relations show that amylin acts as a noncompetitive or functional antagonist of insulin in skeletal muscle (Young et al., *Am. J. Physiol.*, 263(2):E274–E281 (1992)). There is no evidence that amylin interferes with insulin binding to its receptors, or the subsequent activation of insulin receptor tyrosine kinase (Follett et al., *Clinical Research*, 39(1):39A (1991)); Koopmans et al., *Diabetologia*, 34:218–224 (1991)).

It is believed that amylin acts through receptors present in plasma membranes. Studies of amylin and CGRP, and the effect of selective antagonists, suggest that amylin acts via its own receptor (Beaumont et al., *Br. J. Pharmacol.*, 115(5):713–715 (1995); Wang et al., *FEBS Letts.*, 219:195–198 (1991 b)), counter to the conclusion of other workers that amylin may act primarily at CGRP receptors (e.g., Chantry et al., *Biochem. J.*, 277:139–143 (1991)); Galeazza et al., *Peptides*, 12:585–591 (1991)); Zhu et al., *Biochem. Biophys. Res. Commun.*, 177(2):771–776 (1991)). Amylin receptors and their use in methods for screening and assaying for amylin agonist and antagonist compounds are described in U.S. Pat. No. 5,264,372, issued Nov. 23, 1993.

While amylin has marked effects on hepatic fuel metabolism in vivo, there is no general agreement as to what amylin actions are seen in isolated hepatocytes or perfused liver. The available data do not support the idea that amylin promotes hepatic glycogenolysis, i.e., it does not act like glucagon (e.g., Stephens et al., *Diabetes*, 40:395–400 (1991); Gomez-Foix et al., *Biochem J.*, 276:607–610 (1991)). It has been suggested that amylin may act on the liver to promote conversion of lactate to glycogen and to enhance the amount of glucose able to be liberated by glucagon (see Roden et al., *Diabetologia*, 35:116–120 (1992)). In this way, amylin could act as an anabolic partner to insulin in liver, in contrast to its catabolic action in muscle.

In fat cells, contrary to its action in muscle, amylin has no detectable actions on insulin-stimulated glucose uptake, incorporation of glucose into triglyceride, $CO_2$ production (Cooper et al., *Proc. Natl. Acad. Sci.*, 85:7763–7766 (1988)) epinephrine-stimulated lipolysis, or insulin-inhibition of lipolysis (Lupien and Young, "Diabetes Nutrition and Metabolism—Clinical and Experimental," Vol. 6(1), pages 1318 (February 1993)). Amylin thus exerts tissue-specific effects, with direct action on skeletal muscle, marked indirect (via supply of substrate) and perhaps direct effects on liver, while adipocytes appear "blind" to the presence or absence of amylin.

It has also been reported that amylin can have marked effects on secretion of insulin. In isolated islets (Ohsawa et al., *Biochem. Biophys. Res. Commun.*, 160(2):961–967 (1989)), in the perfused pancreas (Silvestre et al., *Reg. Pept.*, 31:23–31 (1991)), and in the intact rat (Young et al., *Mol. Cell. Endocrinol.*, 84:R1–R5 (1992)), some experiments indicate that amylin inhibits insulin secretion. Other workers, however, have been unable to detect effects of amylin on isolated β-cells, on isolated islets, or in the whole animal (see Broderick et al., *Biochem. Biophys. Res. Commun.*, 177:932–938 (1991) and references therein).

Amylin or amylin agonists potently inhibit gastric emptying in rats (Young et al., *Diabetologia* 38(6):642–648 (1995)), dogs (Brown et al., *Diabetes* 43(Suppl 1):172A (1994)) and humans (Macdonald et al., *Diabetologia* 38(Suppl 1):A32 (abstract 118)(1995)). Gastric emptying is reportedly accelerated in amylin-deficient type 1 diabetic BB rats (Young et al., *Diabetologia*, supra; Nowak et al., *J. Lab. Clin. Med.*, 123(1):110–6 (1994)) and in rats treated with the selective amylin antagonist, AC187 (Gedulin et al., *Diabetologia*, 38(Suppl 1):A244 (1995). The effect of amylin on gastric emptying appears to be physiological (operative at concentrations that normally circulate).

Non-metabolic actions of amylin include vasodilator effects which may be mediated by interaction with CGRP vascular receptors. Reported in vivo tests suggest that amylin is at least about 100 to 1000 times less potent than CGRP as a vasodilator (Brain et al., *Eur. J. Pharmacol.*, 183:2221 (1990); Wang et al., *FEBS Letts.*, 291:195–198 (1991)). The effect of amylin on regional hemodynamic actions, including renal blood flow, in conscious rats has been reported (Gardiner et al., *Diabetes*, 40:948–951 (1991)). The authors noted that infusion of rat amylin was associated with greater renal vasodilation and less mesenteric vasoconstriction than is seen with infusion of human α-CGRP. They concluded that, by promoting renal hyperemia to a greater extent than did α-CGRP, rat amylin could cause less marked stimulation of the renin-angiotensin system, and thus, less secondary angiotensin II-mediated vasoconstriction. It was also noted, however, that during coninfusion of human $\alpha\text{-}^{8\text{-}37}$CGRP and rat amylin, renal and mesenteric vasoconstrictions were unmasked, presumably due to unopposed vasoconstrictor effects of angiotensin II, and that this finding is similar to that seen during coinfusion of human A-CGRP and human $\alpha\text{-}^{8\text{-}37}$CGRP (id. at 951).

Injected into the brain, or administered peripherally, amylin has been reported to suppress food intake, e.g., Chance et al., *Brain Res.*, 539:352–354 (1991)), an action shared with CGRP and calcitonin. The effective concentrations at the cells that mediate this action are not known. Amylin has also been reported to have effects both on isolated osteoclasts where it caused cell quiescence, and in vivo where it was reported to lower plasma calcium by up to 20% in rats, in rabbits, and in humans with Paget's disease (see, e.g., Zaidi et al., *Trends in Endocrinol. and Metab.*, 4:255–259 (1993). From the available data, amylin seems to be 10 to 30 times less potent than human calcitonin for these actions. Interestingly, it was reported that amylin appeared to increase osteoclast cAMP production but not to increase cytosolic $Ca^{2+}$, while calcitonin does both (Alam et al., *Biochem. Biophys. Res. Commun.*, 179(1):134–139 (1991)). It was suggested, though not established, that calcitonin may act via two receptor types and that amylin may interact with one of these.

It has also been discovered that, surprisingly in view of its previously described renal vasodilator and other properties, amylin markedly increases plasma renin activity in intact rats when given subcutaneously in a manner that avoids any disturbance of blood pressure. This latter point is important because lowered blood pressure is a strong stimulus to renin release. Amylin antagonists, such as amylin receptor antagonists, including those selective for amylin receptors compared to CGRP and/or calcitonin receptors, can be used to block the amylin-evoked rise of plasma renin activity. The use of amylin antagonists to treat renin-related disorders is described in U.S. Pat. No. 5,376,638, issued Dec. 27, 1994.

In normal humans, fasting amylin levels from 1 to 10 pM and post-prandial or post-glucose levels of 5 to 20 pM have been reported (e.g., Hartter et al., *Diabetologia*, 34:52–54 (1991); Sanke et al., *Diabetologia*, 34:129–132 (1991); Koda et al., *The Lancet*, 339:1179–1180 (1992)). In obese, insulin-resistant individuals, post-food amylin levels can go higher, reaching up to about 50 pM. For comparison, the values for fasting and post-prandial insulin are 20 to 50 pM, and 100 to 300 pM respectively in healthy people, with perhaps 3-to 4-fold higher levels in insulin-resistant people. In Type 1 diabetes, where beta cells are destroyed, amylin levels are at or below the levels of detection and do not rise in response to glucose (Koda et al., *The Lancet*, 339:1179–1180 (1992)). In normal mice and rats, basal amylin levels have been reported from 30 to 100 pM, while values up to 600 pM have been measured in certain insulin-resistant, diabetic strains of rodents (e.g., Huang et al., *Hypertension*, 19:I-101-I-109 (1991); Gill et al., *Life Sciences*, 48:703–710 (1991)).

Pain

Pain is defined by the International Association for the Study of Pain as "an unpleasant sensory and emotional experience associated with actual or potential tissue damage, or described in terms of such damage." Merskey, *Pain* 6:249 (1979). Many diseases and medical procedures are characterized by the sense of pain in different ways for a patient. For example, during and after surgical operations, the manifestation of pain is high. The same is true for many disorders involving trauma, such as burns. Pain is also present in most inflammatory conditions and in association with tumor-related diseases or their treatment. Different therapies are used to achieve an analgesic effect. Drugs such as narcotic analgesics, for example, morphine, are used for reducing severe pain, for example that associated with surgical operations. Other pharmaceuticals used to reduce pain are sedative agents, which include barbiturates and benzodiazepines. Many of these drugs have side effects such as depressant action on respiration and circulation. Several of these drugs also may induce hypnotic effects. Nonsteroidal drugs are also used to treat pain and inflammation, and appear to act by preventing the synthesis of prostaglandins.

Chronic or intractable pain, such as may occur in conditions such as degenerative bone diseases and cancer, is a debilitating condition which is treated with a variety of analgesic agents, for example, narcotic analgesics compounds such as morphine. Chronic pain can also outlast the onset of any known or suspected physical cause. It can occur long after a known injury or disease or it can occur without any known physical cause whatsoever. It can also be accompanied by known tissue pathology, such as chronic inflammation which occurs in some types of arthritis.

In general, brain pathways governing the perception of pain are incompletely understood. Sensory afferent synaptic connections to the spinal cord, termed "nociceptive pathways" have been documented in some detail. In the first leg of such pathways, C- and A-fibers which project from peripheral sites to the spinal cord carry nociceptive signals. Polysynaptic junctions in the dorsal horn of the spinal cord are involved in the relay and modulation of sensations of pain to various regions of the brain, including the periaqueductal grey region. McGeer et al., *Molecular Neurobiology of the Mammalian Brain*, Plenum Press, New York, 1987. Analgesia, or the absence or reduction of pain in response to a stimulation that would normally be painful, can be effected directly by decreasing transmission along such nociceptive pathways. Analgesic opiates are thought to act by mimicking the effects of endorphin or enkephalin peptide-containing neurons, which terminate presynaptically at the C- or A-fiber terminals and which, when they fire, inhibit release of substance P.

Narcotic analgesics, for example, opiates such as morphine, while effective in producing analgesia, may induce tolerance in a subject, so that increasing doses are required to achieve a satisfactory effect. At high doses, such compounds may produce side effects, including respiratory depression, which can be life threatening, and/or nausea and vomiting, which are unpleasant and can be life-threatening in a sedated patient. Such compounds may also produce physical dependence in a subject. Dependence appears to be related to the dose of narcotic analgesic taken and the period of time over which it is taken. Therefore, compounds which serve as either a replacement for, or as an adjunct to, narcotic analgesic treatment have utility in, and would be of significant value for, the treatment of pain, particularly pain of the chronic type.

SUMMARY OF THE INVENTION

We have now discovered, surprisingly, and despite contrary reports from others (see, e.g., Bouali et al, *Regul. Peptides* 56:167–174 (1995), that amylin, as well as amylin agonists, for example, the amylin agonist analogue $^{25,28,29}$Pro-h-amylin (also referred to as "pramlintide" and previously referred to as "AC-0137"), can be used for analgesia in mammals.

The present invention is directed to novel methods for treating pain comprising the administration of an amylin or an amylin agonist, for example, the amylin agonist analogue $^{25,28,29}$Pro-h-amylin, wherein the agonist is not a calcitonin. By "calcitonin" is meant the human peptide hormone calcitonin and species variations of it, such as rat calcitonin, salmon calcitonin and eel calcitonin (including aminosuberic eel calcitonin). In one aspect, the invention is directed to a method of treating pain in a mammalian subject comprising administering to said subject an effective analgesic amount of an amylin or such an amylin agonist. By "effective analgesic amount" is meant an amount effective to reduce or eliminate pain in response to a stimulation that would normally be painful, and thus includes a complete analgesic effect (absence of pain) as well as what is sometimes referred to as "hypalgesic" effect or reduction in pain.

The term "amylin" is understood to include compounds such as those defined in U.S. Pat. No. 5,234,906, issued Aug. 10, 1993, for "Hyperglycemic Compositions," the contents of which are hereby incorporated by reference. For example, it includes the human peptide hormone referred to as amylin and secreted from the beta cells of the pancreas, and species variations of it.

"Amylin agonist" is also a term known in the art, and refers to a compound which mimics effects of amylin. An amylin agonist may be a peptide or a non-peptide compound, and includes amylin agonist analogues.

The term "amylin agonist analogue" is understood to refer to derivatives of an amylin which act as amylin agonists, normally, it is presently believed, by virtue of binding to or otherwise directly or indirectly interacting with an amylin receptor or other receptor or receptors with which amylin itself may interact to elicit a biological response. Useful amylin agonist analogues include those identified in an International Application, WPI Acc. No. 93-182488/22, entitled "New Amylin Agonist Peptides Used for Treatment and Prevention of Hypoglycemia and Diabetes Mellitus," the contents of which is also hereby incorporated by reference.

In a preferred embodiment, the amylin agonist is an amylin agonist analogue, preferably, $^{25,28,29}$Pro-h-amylin. In yet other preferred embodiments, the method further comprises administering a narcotic analgesic or other pain relief agent. By "narcotic analgesic" is meant the naturally occurring opium alkaloids, semi-synthetic and synthetic derivatives. Examples of such compounds include morphine, pentazocine, hydromorphone, oxymorphone, levorphanol, methadone, meperidine, anileridine, alphaprodine, fentanol, codeine, oxycodone and hydrocordone. Preferred narcotic analgesics include morphine and pentazocine.

In another aspect, the invention is directed to a method of enhancing the analgesic activity of a narcotic analgesic comprising administering said narcotic analgesic along with an amylin or an amylin agonist as described herein. This co-administration enables the use of lower doses of either or both drugs with a concomitant reduction in the risk of possible side effects. Such co-administration may be performed by administering such a narcotic analgesic and such amylin or amylin agonist either separately or together. In a preferred embodiment, the amylin agonist is an amylin agonist analogue, preferably, $^{25,28,29}$Pro-h-amylin.

In a related aspect, the invention features pharmaceutical compositions comprising a therapeutically effective amount of a mixture of (1) an amylin and/or an amylin agonist as described herein, preferably, the amylin agonist analogue, $^{25,28,29}$Pro-h-amylin, and (2) a narcotic analgesic or other pain relief agent.

Such compositions may include pharmaceutically acceptable salts of amylin or an amylin agonist, and/or pharmaceutically acceptable salts of a narcotic analgesic or other pain relief agent. Such compositions may further comprise a pharmaceutically acceptable carrier.

The use of amylin or an amylin agonist, having vasodilator activity, either alone or in combination with a narcotic analgesic or other pain relief agent, will be especially useful in the treatment of vascular headache, such as migraine.

DETAILED DESCRIPTION OF THE INVENTION

Figure 1:
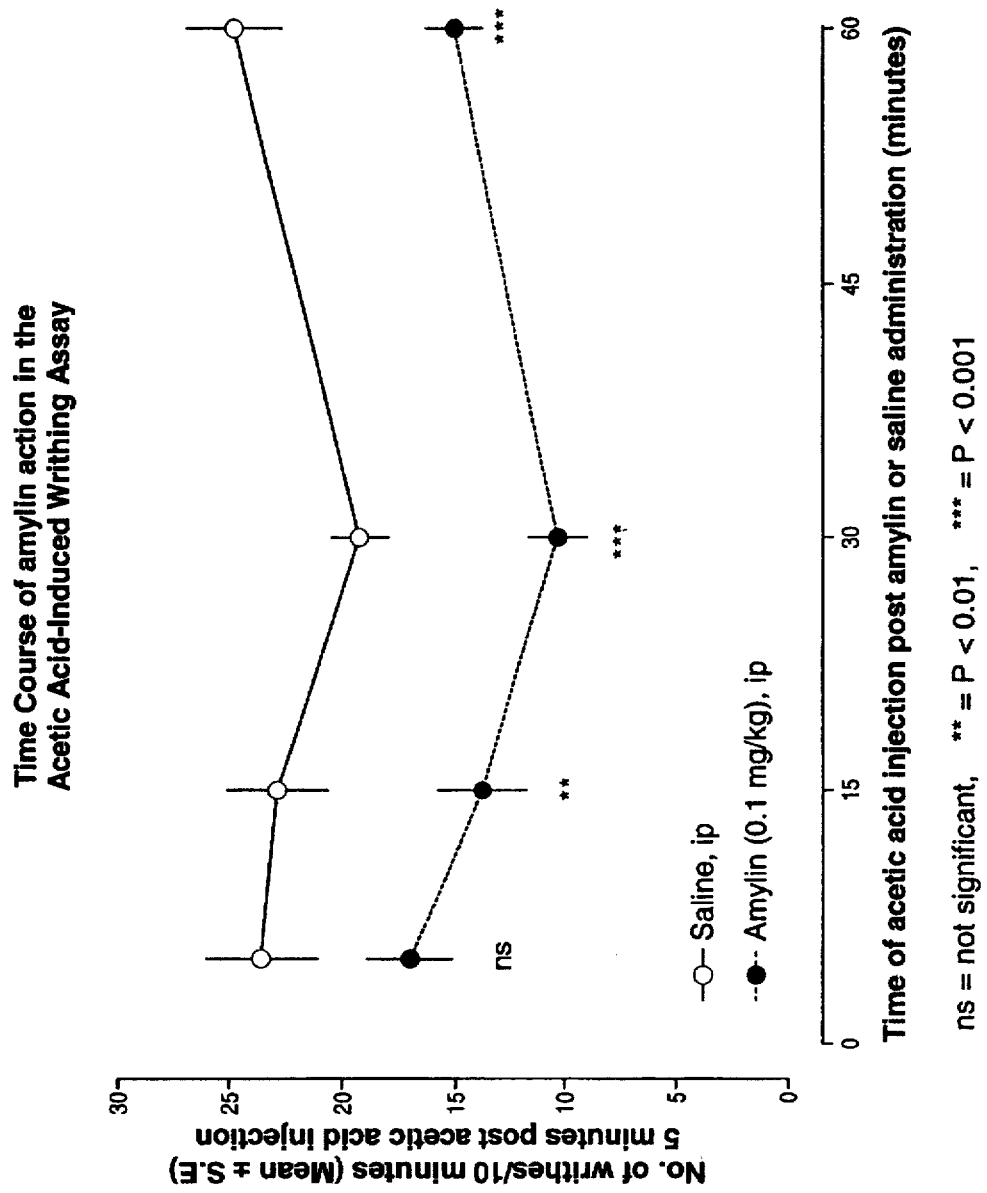
FIG. 1 shows the results of a time course study of the effect of amylin administration on number of writhes per 10 minutes, 5 minutes after acetic acid administration when 0.1 mg/kg amylin (closed circles) or saline (open circles) was injected intraperitoneally (ip) 5, 15, 30 and 60 minutes prior to acetic acid injection in mice. The error bars indicate mean±standard error.
Figure 2:
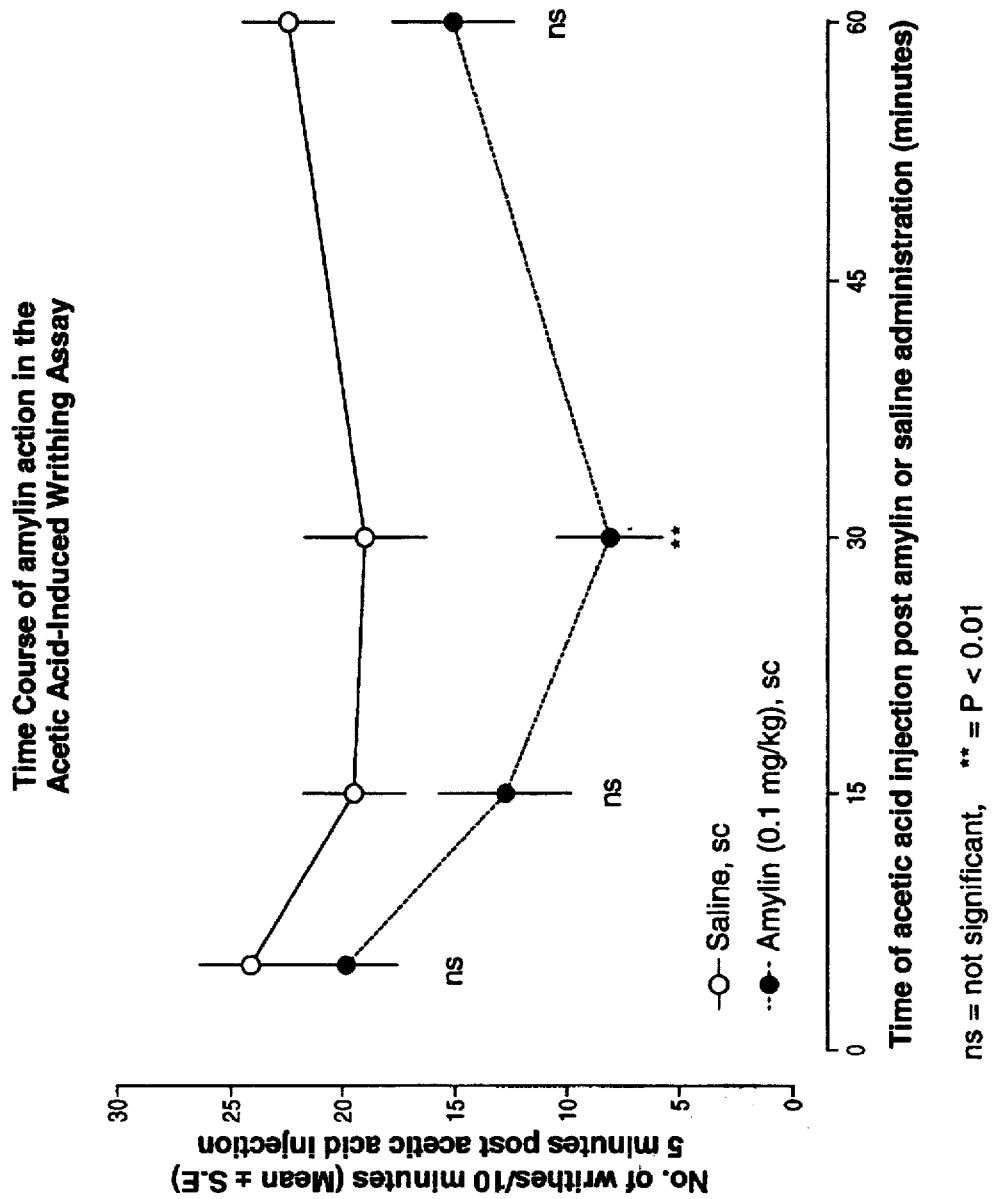
FIG. 2 shows the results of a time course study of the effect of amylin administration on number of writhes per 10 minutes, 5 minutes after acetic acid administration when 0.1 mg/kg amylin (closed circles) or saline (open circles) was injected subcutaneously (sc) 5, 15, 30 and 60 minutes prior to acetic acid injection in mice. The error bars indicate mean±standard error.

The rate of writhing activity in response to intraperitoneal injection of dilute acetic acid in mice is a commonly used surrogate of pain in animal studies of analgesia. As described in Example 1, rat amylin, when injected 30 minutes prior to acetic acid injection (both intraperitoneally and subcutaneously) in mice, significantly reduced the number of writhes in the 10-minute period beginning 5 minutes after acetic acid injection compared to control ($P<0.001$ for ip injection; $P<0.01$ for sc injection). As indicated in FIGS. 1 and 2, the peak analgesic effect of amylin occurred when administered 30 minutes prior to acetic acid injection. Based on these studies, a 30-minute time point was selected for use in dose response studies.

Example 2 shows the analgesic effect of various doses of amylin. The results shown FIGS. 3 and 4 indicate that the lowest effective dose of amylin in these experiments was 0.01 mg/kg ($P<0.05$ sc; $P<0.01$ ip). A 0.1 mg/kg dose of amylin was also effective in inducing analgesia ($P<0.01$ sc; $P<0.05$ ip). At higher doses (1 mg/kg and 10 mg/kg), amylin did not show significant analgesic activity in this model ($P<0.05$). These examples demonstrate the effectiveness of amylin, as well as amylin agonists including amylin agonist analogues, in averting nociceptive behavior (writhing) in mice injected with acetic acid. These results also indicate that the analgesic effectiveness of amylin or amylin agonists may be dose-dependent.

Figure 5:
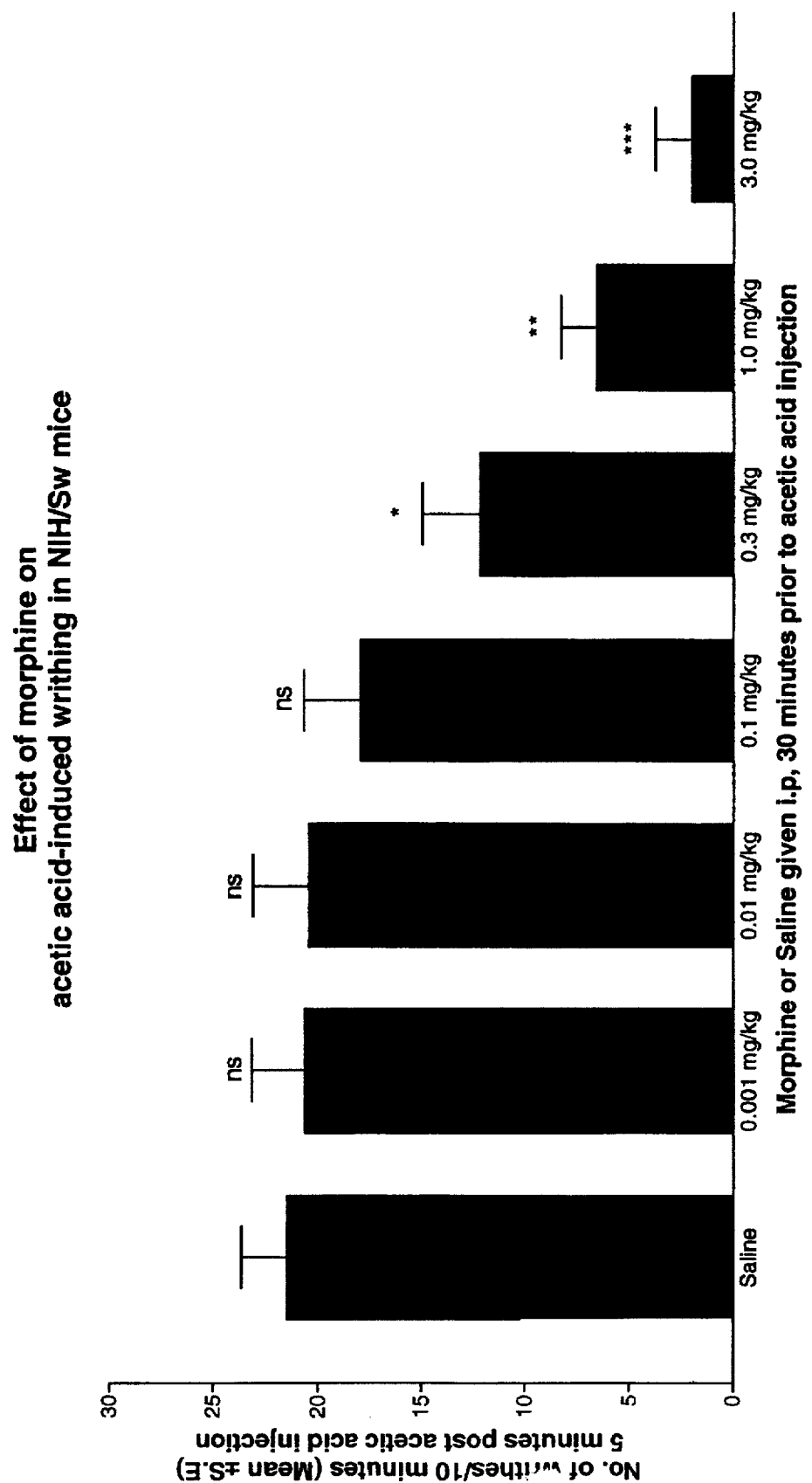
FIG. 5 shows the results of a dose response study of the effect of administration of various doses (0.001 mg/kg, 0.1 mg/kg, 0.3 mg/kg, 1.0 mg/kg and 3.0 mg/kg) of morphine on the number of writhes per 10 minutes, 5 minutes after acetic acid administration when injected subcutaneously (sc) 30 minutes prior to acetic acid injection in mice. The error bars indicate mean±standard error.

Example 3 describes an experiment in which various doses of morphine were tested for analgesic activity, using the same mouse writhing assay procedures as in Examples 1 and 2. As shown in FIG. 5, dosages of 0.3 mg/kg, 1.0 mg/kg and 3.0 mg/kg were effective in inducing analgesia under these experimental conditions.

Figure 6:
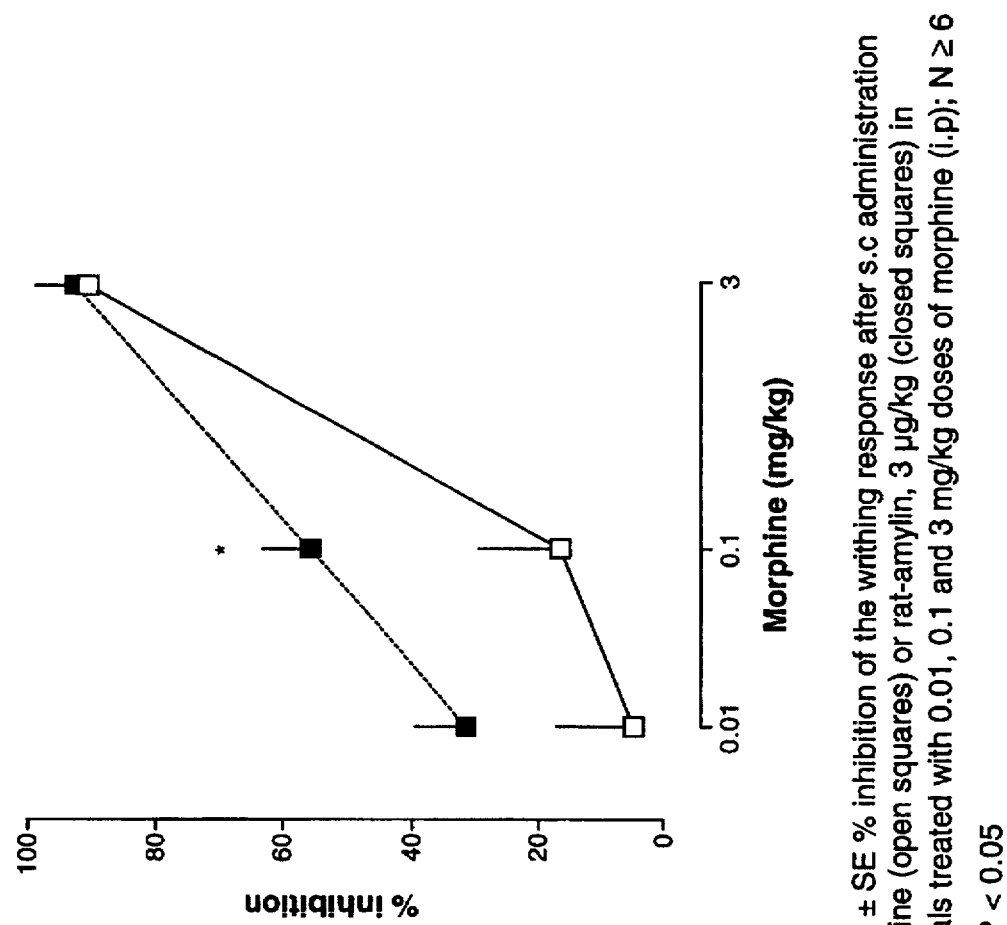
FIG. 6 shows the percent inhibition (mean±standard error) of number of writhes per 10 minutes, 5 minutes after acetic acid administration, in mice injected subcutaneously (sc) with 0.003 mg/kg amylin (closed squares) or saline (open squares) in animals treated with various doses (0.01 mg/kg, 0.1 mg/kg or 3.0 mg/kg) of morphine.
Figure 7:
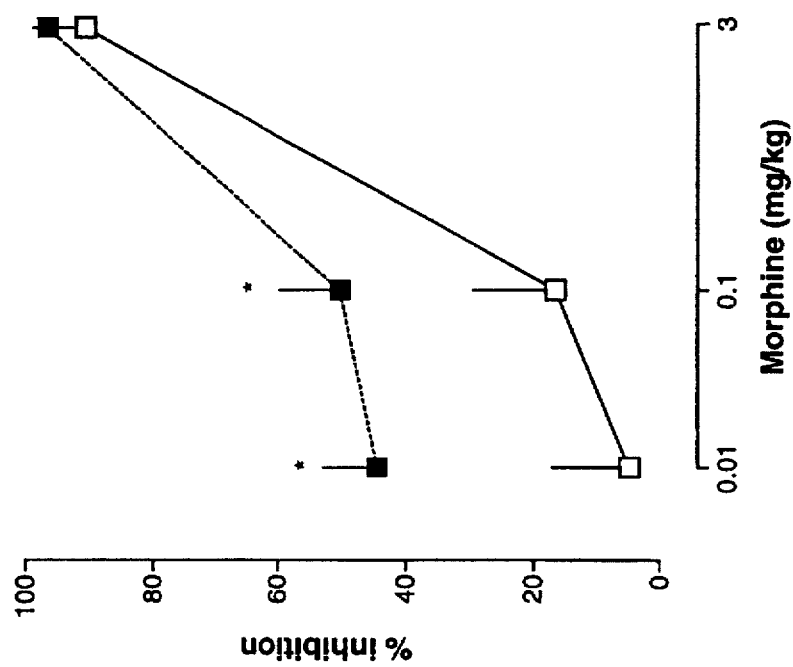
FIG. 7 shows the percent inhibition (mean±standard error) of number of writhes per 10 minutes, 5 minutes after acetic acid administration, in mice injected subcutaneously (sc) with 0.01 mg/kg amylin (closed squares) or saline (open squares) in animals treated with various doses (0.01 mg/kg, 0.1 mg/kg or 3.0 mg/kg) morphine.

Example 4 describes experiments in which the analgesic activity of various dosages of amylin and morphine was examined, the same mouse writhing assay procedures as in the previous Examples. In one study, a dose of rat amylin which had been shown to be ineffective (0.003 mg/kg) in inducing analgesia under the experimental conditions in Example 2 was combined with three doses of morphine: 0.01 mg/kg, 0.1 mg/kg and 3.0 mg/kg. In another study, a dose of rat amylin which had been shown to be effective (0.01 mg/kg) in inducing analgesia under the experimental conditions in Example 2 was combined with the same three doses of morphine. Amylin plus morphine showed an increased efficacy in reducing analgesia compared to morphine alone at combinations of: (1) 0.003 mg/kg amylin plus 0.1 mg/kg morphine ($P<0.05$); (2) 0.01 mg/kg amylin plus 0.01 mg/kg morphine ($P<0.05$); and (3) 0.01 mg/kg amylin plus 0.1 mg/kg morphine ($P<0.05$). Additionally, a combination of a non-analgesic dose of amylin (0.003 mg/kg) and a non-analgesic dose of morphine (0.1 mg/kg) were shown to together provide an analgesic effect. The data are shown in FIGS. 6 and 7.

Figure 8:
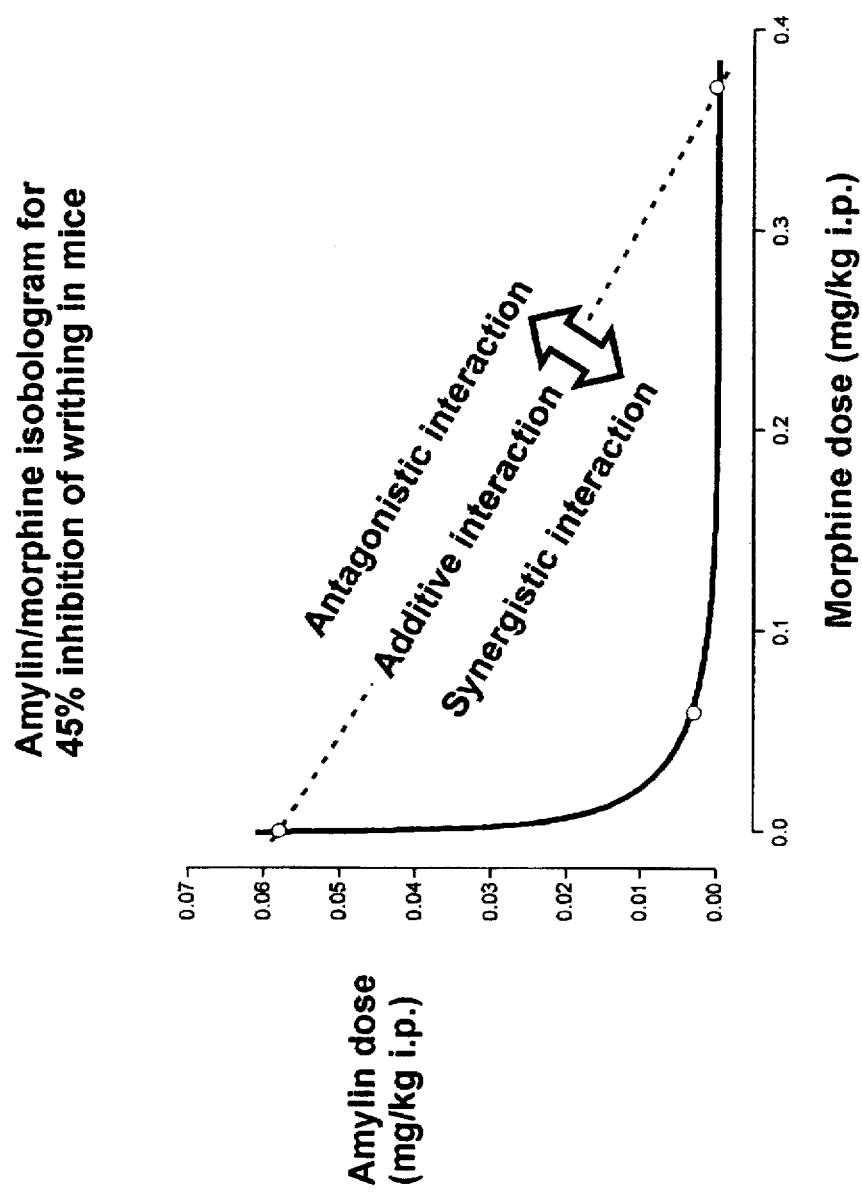
FIG. 8 is an isobologram plot characterizing 45% inhibition of the writhing response (number of writhes per 10 minutes, 5 minutes after acetic acid administration when injected 30 minutes prior to acetic acid injection in mice). The data shown in this plot are taken from FIGS. 2, 5, 6 and 7.

Example 5 describes analysis of the results of the writhing studies of Examples 2–4 to further characterize the interaction between amylin and morphine. The results were graphed in isobolograms according to the method of Berebaum, *J. Theor. Biol.* 144:413 (1985). The isobologram is a quantitative method for measuring interactions between equieffective dosages of drugs to indicate synergy, additive effect or antagonism. As shown in FIG. 8, the interaction of amylin and morphine on acetic acid-induced writhing in mice is synergistic. That is, the resulting activity of amylin and morphine together is greater than the sum of the activities of the individual components.

Figure 9:
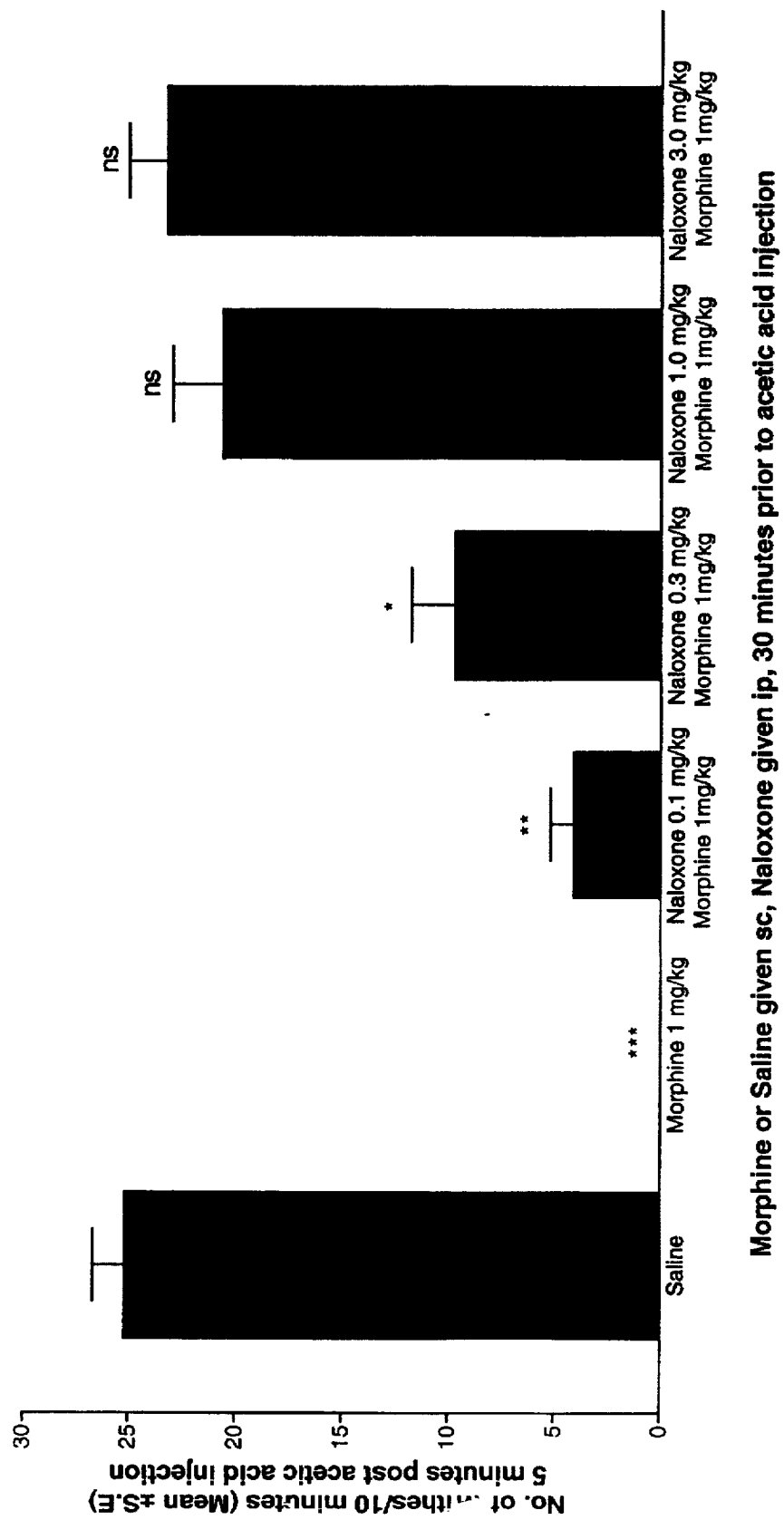
FIG. 9 shows the results of a dose response study of the effect of the administration of various doses (0.1 mg/kg, 0.3 mg/kg, 1.0 mg/kg and 3.0 mg/kg) of naloxone, which acts as a morphine antagonist, with morphine (1 mg/kg) on the number of writhes per 10 minutes, 5 minutes after acetic acid administration when injected 30 minutes prior to acetic acid injection in mice. The error bars indicate mean±standard error.
Figure 10:
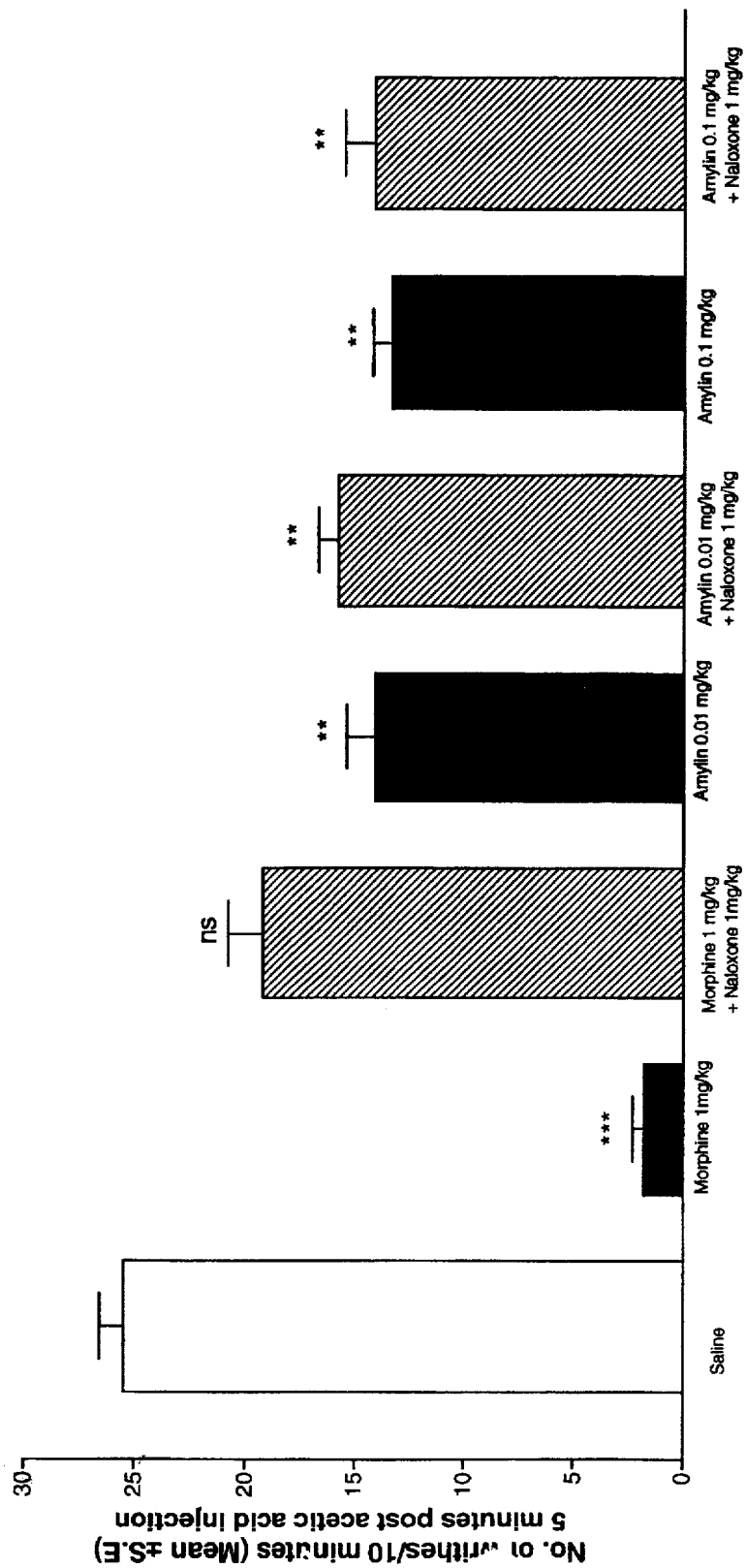
FIG. 10 shows the results of a study of the effect of the administration of morphine (1.0 mg/kg) with or without naloxone (1 mg/kgl) or amylin (0.01 mg/kg or 0.1 mg/kg) with or without naloxone (1 mg/kg) number of writhes per 10 minutes, 5 minutes after acetic acid administration when injected 30 minutes prior to acetic acid injection in mice, indicating the effect of naloxone on morphine- and amylin-induced analgesia. The error bars indicate mean±standard error.

Example 6 describes experiments in which the effect of the morphine antagonist, naloxone, was examined for its ability to counteract morphine-induced analgesia and amylin-induced analgesia in the mouse writhing assay described above. As shown in FIGS. 9 and 10, while 1.0 mg/kg naloxone was effective in counteracting the analgesic effect of 1.0 mg/kg morphine, it was ineffective in counteracting the effect of amylin (0.01 mg/kg and 1.0 mg/kg) on analgesia, indicating that morphine and amylin act by different mechanisms in inducing analgesia.

As described in Example 7, additional narcotic analgesics are evaluated following the methods of Examples 1–6.

Amylin agonist analogues useful in this invention include amylin agonist analogues disclosed in the above-noted WPI Acc. No. 93-182488/22, "New Amylin Agonist Peptides Used for Treatment and Prevention of Hypoglycemia and Diabetes Mellitus." Preferred amylin agonist analogues include 25,28,29Pro-h-amylin, $^{18}$Arg$^{25,28,29}$Pro-h-amylin and $^{18}$Arg$^{25,28}$Pro-h-amylin.

Activity as amylin agonists can be confirmed and quantified by performing various screening assays, including the nucleus accumbens receptor binding assay described below in Example 11, followed by the soleus muscle assay described below in Example 12, a gastric emptying assay described below in Example 13 or 14, or by the ability to induce hypocalcemia or reduce postprandial hyperglycemia in mammals, as described herein.

The receptor binding assay, a competition assay which measures the ability of compounds to bind specifically to membrane-bound amylin receptors, is described in U.S. Pat. No. 5,264,372, issued Nov. 23, 1993, the disclosure of which is incorporated herein by reference. The receptor binding assay is also described in Example 11 below. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et al. (ALLFIT, Version 2.7 (NIH, Bethesda, Md. 20892)). Munson and Rodbard, *Anal. Biochem.* 107:220–239 (1980).

Assays of biological activity of amylin agonists in the soleus muscle may be performed using previously described methods (Leighton, B. and Cooper, *Nature,* 335:632–635 (1988); Cooper, et al., *Proc. Natl. Acad. Sci. USA* 85:7763–7766 (1988)), in which amylin agonist activity may be assessed by measuring the inhibition of insulin-stimulated glycogen synthesis. The soleus muscle assay is also described in Example 12 below.

Methods of measuring the rate of gastric emptying are disclosed in, for example, Young et al., *Diabetologia,* 38(6):642–648 (1995). In a phenol red method, which is described in Example 13 below, conscious rats receive by gavage an acoloric gel containing methyl cellulose and a phenol red indicator. Twenty minutes after gavage, animals are anesthetized using halothane, the stomach exposed and clamped at the pyloric and lower esophageal sphincters, removed and opened into an alkaline solution. Stomach content may be derived from the intensity of the phenol red in the alkaline solution, measured by absorbance at a wavelength of 560 nm. In a tritiated glucose method, which is described in Example 14 below, conscious rats are gavaged with tritiated glucose in water. The rats are gently restrained by the tail, the tip of which is anesthetized using lidocaine. Tritium in the plasma separated from tail blood is collected at various timepoints and detected in a beta counter. Test compounds are normally administered about one minute before gavage.

Effects of amylins or amylin agonists on pain can be identified, evaluated, or screened for using the methods described in Examples 1–5 below, or other art-known or equivalent methods for determining analgesic effect. See, e.g., Tjolsen, et al., *Handbook of Lab Animal Science,* Vol. II, Chapter 12, Animal Models in Pain Research (Svendsen, Ed., CRC Press, 1994). Preferred, amylin agonist compounds exhibit activity in the receptor binding assay on the order of less than about 1 to 5 nM, preferably less than about 1 nM and more preferably less than about 50 pM. In the soleus muscle assay, preferred amylin agonist compounds show $EC_{50}$ values on the order of less than about 1 to 10 micromolar. In the gastric emptying assays, preferred agonist compounds show $ED_{50}$ values on the order of less than 100 µg/rat.

Amylin and peptide amylin agonists may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu (Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, methylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and Tboc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6–12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac). Solvents (A=0.1% TFA/water and B=0.1% TFA/CH$_3$CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20–24 h). Hydrolysates may be derivatized and analyzed by standard methods (Cohen, et al., *The Pico Tag Method: A Manual of Advanced Techniques for Amino Acid Analysis*, pp. 11–52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989). Non-peptide compounds useful in the present invention may be prepared by art-known methods.

The compounds referenced above may form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Compositions useful in the invention may conveniently be provided in the form of formulations suitable for parenteral (including intravenous, intramuscular and subcutaneous) or nasal or oral administration. In some cases, it will be convenient to provide an amylin agonist and another analgesic agent, for example, an opiate, such as morphine, in a single composition or solution for administration together. In other cases, it may be more advantageous to administer another analgesic agent separately from said amylin or amylin agonist. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds provided as parenteral compositions for injection or infusion can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an amylin or amylin agonist, for example, an amylin agonist analogue compound with or without another analgesic agent which will be effective in one or multiple doses to control pain at the selected level. Therapeutically effective amounts of an amylin or amylin agonist, such as an amylin agonist analogue, for use in the control of pain are those that decrease pain. As will be recognized by those in the field, an effective amount of therapeutic agent will vary with many factors including the age and weight of the patient, the patient's physical condition, the action to be obtained and other factors.

The effective single, divided or continuous analgesic doses of the compounds, for example, including $^{25,28,29}$Pro-h-amylin, $^{18}$Arg$^{25,28,29}$Pro-h-amylin and $^{18}$Arg$^{25,28}$Pro-h-amylin will typically be in the range of 0.01 or 0.03 to about 5 mg/day, preferably about 0.01 or 0.5 to 2 mg/day and more preferably about 0.01 or 0.1 to 1 mg/day, for a 70 kg patient, administered in a single, divided or continuous doses. The exact dose to be administered is determined by the attending clinician and is dependent upon a number of factors, including, these noted above. Administration should begin at the first sign of pain. Administration may be by injection or infusion, preferably intravenous, subcutaneous or intramuscular. Orally active compounds may be taken orally, however dosages should be increased 5–10 fold.

Generally, in treating or preventing pain, the compounds of this invention may be administered to patients in need of such treatment in a dosage ranges similar to those given above, however, the compounds may be administered more frequently, for example, one, two, or three times a day or continuously.

To assist in understanding the present invention, the following Examples are included which describe the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Time Course of Amylin Action

Male Swiss Webster mice (NIH/Sw) obtained from Harlan (Madison, Wis.) and weighing 20–35 g were group housed with free access to food and water and maintained in a stable environment (12:12 light:dark cycle; 23°±1° C.). All animals were habituated to the test room for at least one day prior to any experimentation, and were tested once between 07:30 and 14:00.

Rat amylin was synthesized by standard solid phase peptide synthesis methods. Morphine was obtained from Steris Laboratories (Phoenix, Ariz.). All drugs were dissolved in physiological saline, and given in a dose volume 10 ml/kg body weight.

The mouse writhing assay procedure used was a modification of a procedure disclosed in Hendershot and Forsaith, *J. Pharmacol. Expt. Therap.*, 125:237–240 (1959). Each mouse was allowed to habituate to the observation box for at least 15 minutes prior to testing. Each mouse was given an intraperitoneal injection of a 2% acetic acid solution to produce a writhing reaction, characterized by a wave on contraction of the abdominal musculature followed by the extension of the hind limbs. The number of writhes per animal was counted during a 10-minute interval starting 5 minutes after acetic acid injection.

0.1 mg/kg of rat amylin was administered subcutaneously (sc) or intraperitoneally (ip) at 5, 15, 30 and 60 minutes prior to acetic acid injection in mice. Saline injections were used as a negative control.

The results are shown in FIGS. 1 and 2. Amylin, when injected 30 minutes prior to acetic acid injection (both ip and sc), significantly reduced the number of writhes per 10-minute period 5 minutes post acetic acid injection compared to the saline-treated animals ($P<0.001$ for ip injection; $P<0.01$ for sc injection). The peak effect of amylin occurred when administered 30 minutes prior to acetic acid injection. The 30-minute timepoint was selected for use in the dose response studies described in Example 2 below.

EXAMPLE 2

Dose Response of Amylin Action

Figure 3:
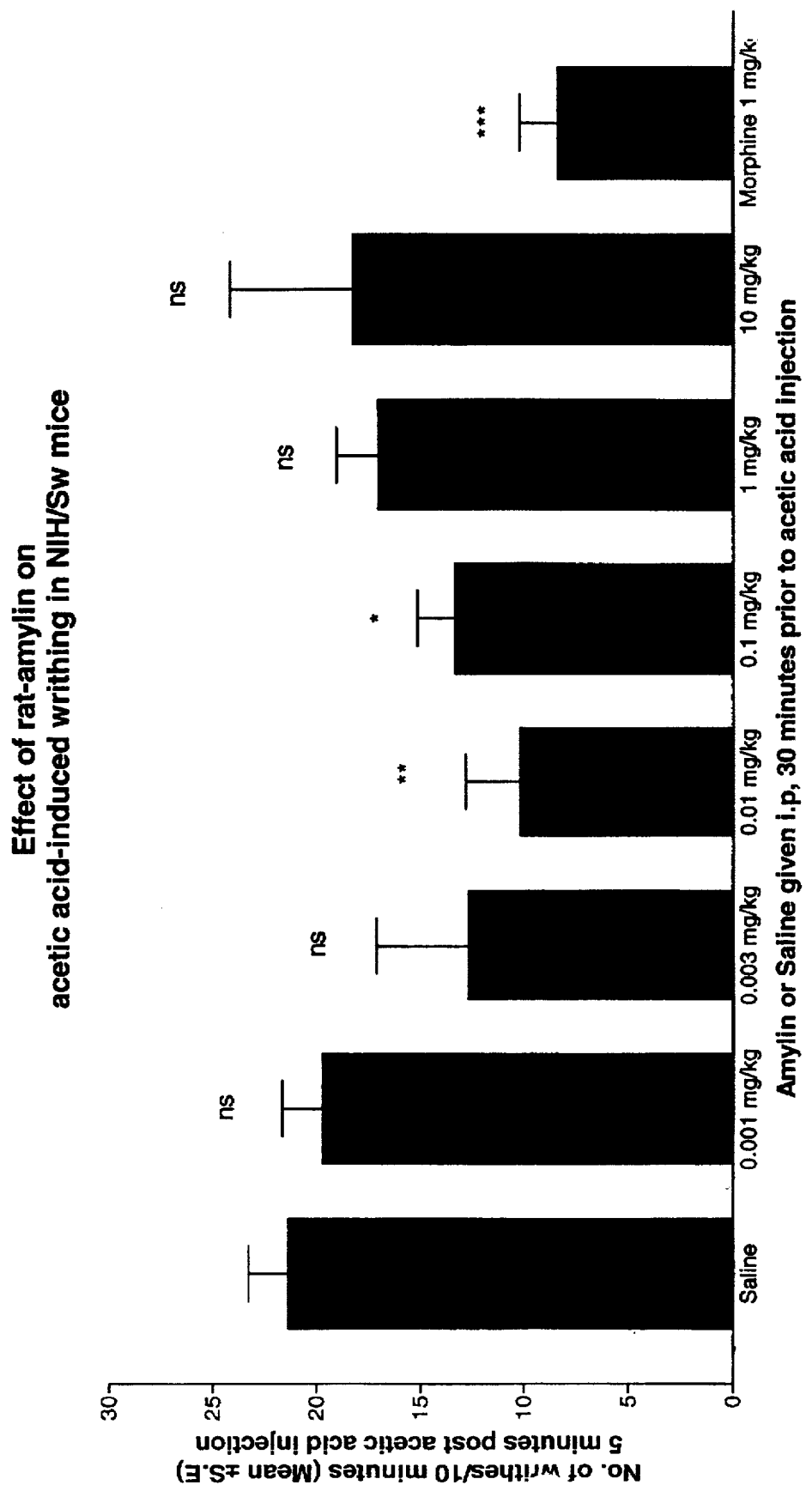
FIG. 3 shows the results of a dose response study of the effect of administration of various doses (0.001 mg/kg, 0.003 mg/kg, 0.01 mg/kg, 1.0 mg/kg and 10.0 mg/kg) of amylin on the number of writhes per 10 minutes, 5 minutes after acetic acid administration when injected intraperitoneally (ip) 30 minutes prior to acetic acid injection in mice. The error bars indicate mean±standard error.
Figure 4:
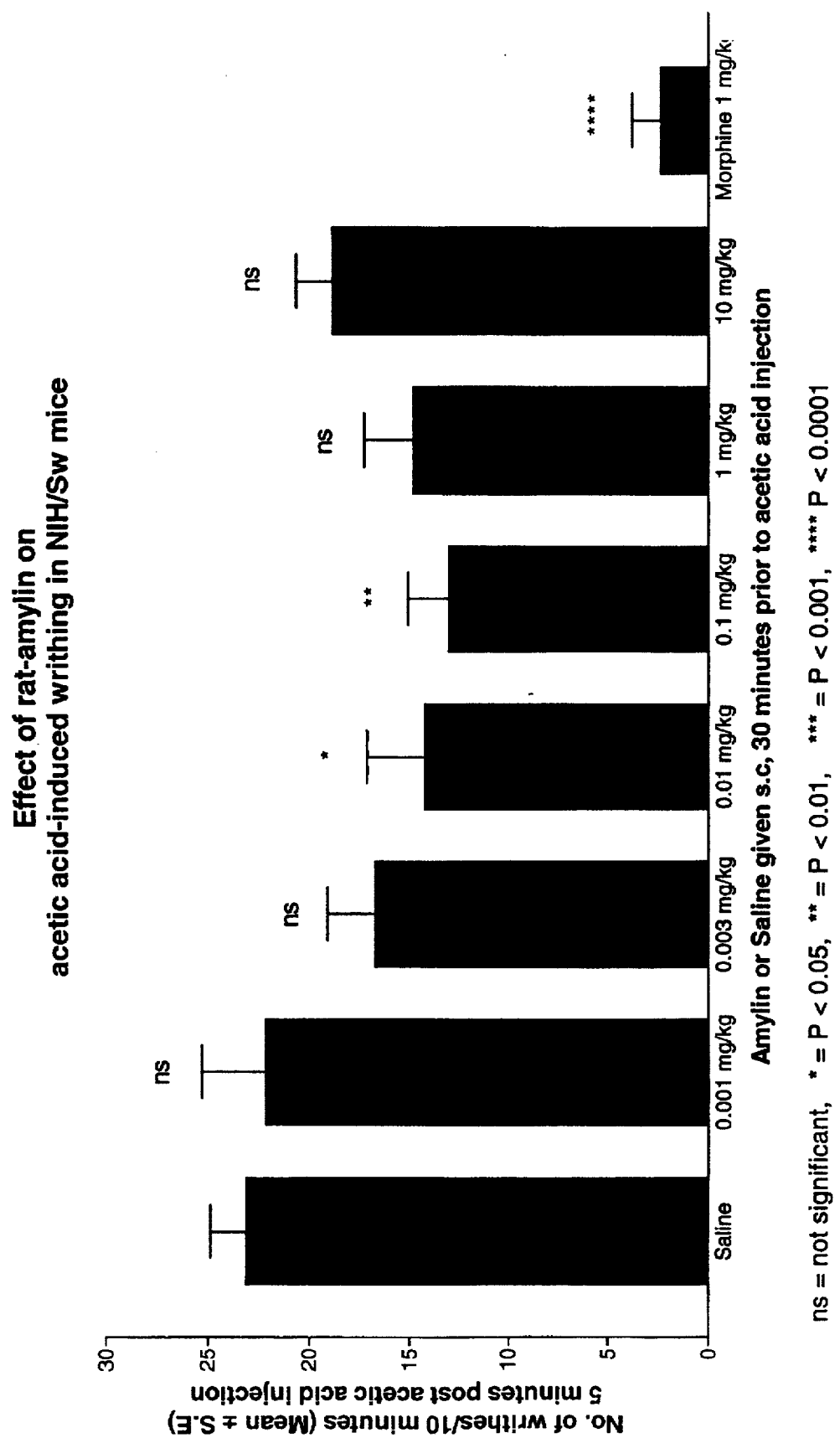
FIG. 4 shows the results of a dose response study of the effect of administration of various doses (0.001 mg/kg, 0.003 mg/kg, 0.01 mg/kg, 1.0 mg/kg and 10.0 mg/kg) of amylin on the number of writhes per 10 minutes, 5 minutes after acetic acid administration when injected subcutaneously (sc) 30 minutes prior to acetic acid injection in mice. The error bars indicate mean±standard error.

The same experimental procedures used in the experiments described in Example 1 were used in the following dose response studies. Subcutaneous and intraperitoneal injections of rat amylin (0.001, 0.003, 0.01, 0.1, 1.0 and 10.0 mg/kg) were given 30 minutes prior to acetic acid injection. Saline was used as a negative control. Morphine (1.0 mg/kg) was used as a positive control. The results are shown in FIGS. 3 and 4. The lowest effective analgesic dose of amylin in these experiments was 0.01 mg/kg ($P<0.05$ sc; $P<0.01$ ip). A dose of 0.1 mg/kg was also effective ($P<0.01$ sc; $P<0.05$ ip). At higher doses administered in this model (1 mg/kg and 10 mg/kg), amylin did not show significant analgesic activity ($P>0.05$).

EXAMPLE 3

Dose Response of Morphine Action

The same experimental procedures used in the experiments described in Example 1 were used in the following dose response studies for morphine. Intraperitoneal injections of morphine (0.001, 0.01, 0.1, 0.3, 1.0 and 3.0 mg/kg) were given 30 minutes prior to acetic acid injection. Saline was used as a negative control. The results are shown in FIG. 5. The lowest effective analgesic dose of morphine in these experiments was 0.3 mg/kg ($P<0.05$). Doses of 1.0 mg/kg and 3.0 mg/kg were also effective ($P<0.01$, $P<0.001$, respectively).

EXAMPLE 4

Analgesic Actions of Amylin and Morphine

The ability of amylin to enhance the analgesic effect of morphine is shown in these experiments, using the same experimental procedures described in Example 1. In one experiment, a dose of rat amylin which had been shown to be ineffective (0.003 mg/kg) in inducing analgesia under the experimental conditions in Example 2 was combined with three doses of morphine: 0.01 mg/kg, 0.1 mg/kg and 3.0 mg/kg (FIG. 6). In another experiment, a dose of rat amylin which had been shown to be effective (0.01 mg/kg) in inducing analgesia under the experimental conditions in Example 2 was combined with the same three doses of morphine (FIG. 7).

Amylin plus morphine showed an increased efficacy in reducing analgesia compared to morphine alone at combinations of: (1) 0.003 mg/kg amylin plus 0.1 mg/kg morphine, $<0.05$ (FIG. 6); (2) 0.01 mg/kg amylin plus 0.01 mg/kg morphine, $P<0.05$ (FIG. 7); and (3) 0.01 mg/kg amylin plus 0.1 mg/kg morphine, $P<0.05$ (FIG. 7). Additionally, a combination of a non-analgesic dose of amylin (0.003 mg/kg) and a non-analgesic dose of morphine (0.1 mg/kg) was shown to provide an analgesic effect.

EXAMPLE 5

Isobologram Analysis of Interaction of Amylin and Morphine

To further characterize the interaction between amylin and morphine, the results of the writhing studies were graphed in isobolograms according to the method of Berebaum, "The expected effect of a combination of agents: the general solution." *J. Theor. Biol.* 114:413 (1985). The isobologram is a quantitative method for measuring interactions between dosages of drugs that are equieffective in relationship to a common pharmacological endpoint to indicate synergy, additive effect or antagonism. In this instance, the writhing test was used to estimate a common level of analgesic dose-ratio combination. The percent of inhibition for each compound and the combination of amylin and morphine were derived from sigmoidal dose-response curves from the data depicted in FIGS. 2, 5, 6 and 7. In an isobologram, areas of dose additional, synergism and antagonism are clearly defined by reference to a theoretical straight (addition) line connecting the points on each axis. According to the isobologram theory, any points falling under the addition line represent enhanced analgesic activity and any points located above the line represent diminished analgesic activity.

The synergistic interaction of amylin and morphine on acetic acid-induced writhing in mice is demonstrated by the data in FIG. 8, in which the analgesic effect of amylin alone is presented on the ordinate and that of morphine alone is presented on the abscissa. The synergistic interaction of amylin and morphine at 45% inhibition of writhing shown in FIG. 8 indicates the existence of unexpectedly enhanced analgesic activity of combinations of amylin and morphine. That is, the resulting activity of amylin and morphine together is greater than the activity expected from the sum of the activities of the individual components.

EXAMPLE 6

Effective of Naloxone on Morphine-Induced and Amylin-Induced Analgesia

Following the mouse writhing study procedures of the previous Examples, the effect of the morphine antagonist, naloxone, on morphine-induced analgesia and on amylin-induced analgesia was examined. In one study, the effect of various doses (0.1 mg/kg, 0.3 mg/kg, 1.0 mg/kg and 3.0 mg/kg) of naloxone, administered along with 1.0 mg/kg of morphine, was examined. As shown in FIG. 9, doses of 1.0 mg/kg and 3.0 mg/kg were effective in counteracting the morphine-induced analgesia (as evidenced by number of writhes per minute).

In another study, the effect of 1.0 mg/kg naloxone (which had been shown to be effective in counteracting morphine-induced analgesia in the previous study) was tested for its ability to counteract amylin-induced analgesia. As shown in FIG. 10, the morphine (1.0 mg/kg) plus naloxone (1.0 mg/kg) response was not significantly different from the saline control response, indicating that naloxone was effective in counteracting morphine-induced analgesia. Also as shown in FIG. 10, the results for 0.01 mg/kg or 1.0 mg/kg amylin with or without 1.0 mg/kg naloxone are significantly different from the saline control, indicating that naloxone was not effective in counteracting amylin-induced analgesia. These results indicate that morphine and amylin act by different mechanisms to induce analgesia.

EXAMPLE 7

Analysis of Additional Narcotic Analgesics

Following the procedures of the previous Examples, the dosing characteristics of additional narcotic analgesics useful to relieve pain when administered with an amylin or an amylin agonists are performed by substituting an equianalgesic amount of each of: hydromorphone, oxymorphone, levorphanol, methadone, meperidine, alphapradine, fentanol, codeine, oxycodone or hydrocordone for the morphine of these Examples.

EXAMPLE 8

Preparation of $^{25,28,29}$Pro-h-Amylin

Solid phase synthesis of $^{25,28,29}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^+$=3,949.

EXAMPLE 9

Preparation of $^{18}$Arg$^{25,28,29}$Pro-h-Amylin

Solid phase synthesis of $^{18}$Arg$^{25,28,29}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{18}$Arg$^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^+$=3,971.

EXAMPLE 10

Preparation of $^{18}$Arg$^{25,28,29}$Pro-h-Amylin

Solid phase synthesis of $^{18}$Arg$^{25,28,29}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{18}$Arg$^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^+$=3,959.

EXAMPLE 11

Receptor Binding Assay

Evaluation of the binding of compounds to amylin receptors was carried out as follows. $^{125}$I-rat amylin (Bolton-Hunter labeled at the N-terminal lysine) was purchased from Amersham Corporation (Arlington Heights, Ill.). Specific activities at time of use ranged from 1950 to 2000 Ci/mmol. Unlabeled peptides were obtained from BACHEM Inc. (Torrance, Calif.) and Peninsula Laboratories (Belmont, Calif.).

Male Sprague-Dawley rats (200–250) grams were sacrificed by decapitation. Brains were removed to cold phosphate-buffered saline (PBS). From the ventral surface, cuts were made rostral to the hypothalamus, bounded laterally by the olfactory tracts and extending at a 45° angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23° C.). Membranes were washed three times in fresh buffer by centrifugation for 15 minutes at 48,000× g. The final membrane pellet was resuspended in 20 mM HEPES buffer containing 0.2 mM phenylmethylsulfonyl fluoride (PMSF).

To measure $^{125}$I-amylin binding, membranes from 4 mg original wet weight of tissue were incubated with $^{125}$I-amylin at 12–16 pM in 20 mM HEPES buffer containing 0.5 mg/ml bacitracin, 0.5 mg/ml bovine serum albumin, and 0.2 mM PMSF. Solutions were incubated for 60 minutes at 23° C. Incubations were terminated by filtration through GF/B glass fiber filters (Whatman Inc., Clifton, N.J.) which had been presoaked for 4 hours in 0.3% poylethyleneimine in order to reduce nonspecific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77%. Competition curves were generated by measuring binding in the presence of $10^{-12}$ to $10^{-6}$M unlabeled test compound and were analyzed by nonlinear regression using a 4-parameter logistic equation (Inplot program; GraphPAD Software, San Diego).

In this assay, purified human amylin binds to its receptor at a measured $IC_{50}$ of about 50 pM. Results for test compounds are set forth in Table I, showing that each of the compounds has significant receptor binding activity.

EXAMPLE 12

Soleus Muscle Assay

Determination of amylin agonist activity of compounds was carried out using the soleus muscle assay as follows. Male Harlan Sprague-Dawley rats of approximately 200 g mass were used in order to maintain mass of the split soleus muscle less than 40 mg. The animals were fasted for 4 hours prior to sacrifice by decapitation. The skin was stripped from the lower limb which was then pinned out on corkboard. The tendo achilles was cut just above os calcis and *M. gastrocnemius* reflected out from the posterior aspect of the tibia. *M. soleus*, a small 15–20 mm long, 0.5 mm thick flat muscle on the bone surface of *M. gastrocnemius* was then stripped clear and the perimysium cleaned off using fine scissors and forceps. *M. soleus* was then split into equal parts using a blade passed antero-posteriorly through the belly of the muscle to obtain a total of 4 muscle strips from each animal. After dissecting the muscle from the animal, it was kept for a short period in physiological saline. It was not necessary that the muscle be held under tension as this had no demonstrable effects on radioglucose incorporation into glycogen.

Muscles were added to 50 mL Erlenmeyer flasks containing 10 mL of a pregassed Krebs-Ringer bicarbonate buffer containing (each liter) NaCl 118.5 mmol (6.93 g), KCl 5.94 mmol (443 mg), $CaCl_2$ 2.54 mmol (282 mg), $MgSO_4$ 1.19 mmol (143 mg), $KH_2PO_4$ 1.19 mmol (162 mg), $NaHCO_3$ 25 mmol (2.1 g), 5.5 mmol glucose (1 g) and recombinant human insulin (Humulin-R, Eli Lilly, Ind.) and the test compound, as detailed below, pH at 37° C. was verified as being between 7.1 and 7.4. Muscles were assigned to different flasks so that the 4 muscle pieces from each animal were evenly distributed among the different assay conditions. The incubation media were gassed by gently blowing carbogen (95% $O_2$, 5% $CO_2$) over the surface while being continuously agitated at 37° C. in an oscillating water bath. After a half-hour "preincubation" period, 0.5 µCi of U-$^{14}$C-glucose was added to each flask which was incubated for a further 60 minutes. Each muscle piece was then rapidly removed, blotted and frozen in liquid $N_2$, weighed and stored for subsequent determination of $^{14}$C-glycogen.

$^{14}$C-glycogen determination was performed in a 7 mL scintillation vial. Each frozen muscle specimen was placed in a vial and digested in 1 mL 60% potassium hydroxide at 70° C. for 45 minutes under continuous agitation. Dissolved glycogen was precipitated out onto the vial by the addition of 3 mL absolute ethanol and overnight cooling at –20° C. The supernatant was gently aspirated, the glycogen washed again with ethanol, aspirated and the precipitate dried under vacuum. All ethanol is evaporated to avoid quenching during scintillation counting. The remaining glycogen was redissolved in 1 mL water and 4 mL scintillation fluid and counted for $^{14}$C.

The rate of glucose incorporation into glycogen (expressed in µmol/g/hr) was obtained from the specific activity of $^{14}$C-glucose in the 5.5 mM glucose of the incubation medium, and the total $^{14}$C counts remaining in the glycogen extracted from each muscle. Dose/response curves were fitted to a 4-parameter logistic model using a least-squares iterative routine (ALLFIT, v2.7, NIH, Md.) to derive $EC_{50}$'s. Since $EC_{50}$ is log-normally distributed, it is expressed±standard error of the logarithm. Pairwise comparisons were performed using t-test based routines of SYSTAT (Wilkinson, "SYSTAT: the system for statistics," SYSTAT Inc., Evanston, Ill. (1989)).

Dose response curves were generated with muscles added to media containing 7.1 nM (1000 µU/mL) insulin and each test compound added at final (nominal) concentrations of 0, 1, 3, 10, 30, 100, 300 and 1000 nM. Each assay also contained internal positive controls consisting of a single batch of archived rat amylin, lyophilized and stored at –70° C.

Human amylin is a known hyperglycemic peptide, and $EC_{50}$ measurements of amylin preparations in the soleus muscle assay range typically from about 1–10 nM, although some commercial preparations which are less than 90% pure have higher $EC_{50}$'s due to the presence of contaminants that result in a lower measured activity. Results for test compounds are set forth in Table I.

TABLE I

| | Receptor Binding Assay $IC_{50}$ (pM) | Soleus Muscle Assay $EC_{50}$ (nM) |
|---|---|---|
| 1) $^{28}$Pro-h-Amylin | 15.0 | 2.64 |
| 2) $^{25}$Pro$^{26}$Val$^{28,29}$Pro-h-Amylin | 18.0 | 4.68 |
| 3) $^{2,7}$Cyclo-[$^2$Asp, $^7$Lys]-h-Amylin | 310.0 | 6.62 |
| 4) $^{2-37}$h-Amylin | 236.0 | 1.63 |
| 5) $^1$Ala-h-Amylin | 148.0 | 12.78 |
| 6) $^1$Ser-h-Amylin | 33.0 | 8.70 |
| 7) $^{29}$Pro-h-Amylin | 64.0 | 3.75 |
| 8) $^{25,28}$Pro-h-Amylin | 26.0 | 13.20 |
| 9) des-$^1$Lys$^{25,28}$Pro-h-Amylin | 85.0 | 7.70 |
| 10) $^{18}$Arg$^{25,28}$Pro-h-Amylin | 32.0 | 2.83 |
| 11) des-$^1$Lys$^{18}$Arg$^{25,28}$Pro-h-Amylin | 82.0 | 3.77 |
| 12) $^{18}$Arg$^{25,28,29}$Pro-h-Amylin | 21.0 | 1.25 |
| 13) des-$^1$Lys$^{18}$Arg$^{25,28,29}$Pro-h-Amylin | 21.0 | 1.86 |
| 14) $^{25,28,29}$Pro-h-Amylin | 10.0 | 3.71 |
| 15) des-$^1$Lys$^{25,28,29}$Pro-h-Amylin | 14.0 | 4.15 |

EXAMPLE 13

PHENOL RED GASTRIC EMPTYING ASSAY

Gastric emptying was measured using a modification (Plourde et al., Life Sci. 53:857–862 (1993)) of the original method of Scarpignato et al. (Arch. Int. Pharmacodyn. Ther. 246:286–295 (1980)). Briefly, conscious rats received by gavage. 1.5 mL of an acoloric gel containing 1.5% methyl cellulose (M-0262, Sigma Chemical Co., St. Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In most experiments, the stomach was clear. In other experiments, particulate gastric contents were centrifuged to clear the solution for absorbance measurements. Where the diluted gastric contents remained turbid, the spectroscopic absorbance due to phenol red was derived as the difference between that present in alkaline vs acetified diluent. In separate experiments on 7 rats, the stomach and small intestine were both excised and opened into an alkaline solution. The quantity of phenol red that could be recovered from the upper gastrointestinal tact within 29 minutes of gavage was 89±4%; dye which appeared to bind irretoverably to the gut luminal surface may have accounted for the balance. To compensate for this small loss, percent of stomach contents remaining after 20 minutes were expressed as a fraction of the gastric contents recovered from control rats sacrificed immediately after gavage in the same experiment. Percent gastric emptying contents remaining=(absorbance at 20 min)/(absorbance at 0 min). Dose response curves for gastric emptying were fitted to a 4-parameter logistic model using a least-squares iterative routine (ALLFIT, v2.7, NIH, Bethesda, Md.) to derive $ED_{50}$s. Since $ED_{50}$ is log-normally distributed, it is expressed±standard error of the logarithm. Pairwise comparisons were performed using one-way analysis of variance and the Student-Newman-Keuls multiple comparisons test (Instat v2.0, GraphPad Software, San Diego, Calif.) using $P<0.05$ as the level of significance.

In dose response studies, rat amylin (Bachem, Torrance, Calif.) dissolved in 0.15M saline, was administered as a 0.1 mL subcutaneous bolus in doses of 0, 0.01, 0.1, 1, 10 or 100 µg 5 minutes before gavage in Harlan Sprague Dawley (non-diabetic) rats fasted 20 hours and diabetic BB rats fasted 6 hours. When subcutaneous amylin injections were given 5 minutes before gavage with phenol red indicator, there was a dose-dependent suppression of gastric emptying (data not shown). Suppression of gastric emptying was complete in normal HSD rats administered 1 µg of amylin, and in diabetic rats administered 10 µg (P=0.22, 0.14). The $ED_{50}$ for inhibition of gastric emptying in normal rats was 0.43 µg (0.60 nmol/kg)±0.19 log units, and was 2.2µ (2.3 nmol/kg)±0.18 log units in diabetic rats.

EXAMPLE 14

TRITIATED GLUCOSE GASTRIC EMPTYING ASSAY

Conscious, non-fasted, Harlan Sprague Dawley rats were restrained by the tail, the tip of which was anesthetized using 2% lidocaine. Tritium in plasma separated from tail blood collected 0, 15, 30, 60, 90 and 120 minutes after gavage was detected in a beta counter. Rats were injected subcutaneously with 0.1 mL saline containing 0, 0.1, 0.3, 1, 10 or 100 µg of rat amylin 1 minute before gavage (n=8,7,5,5,5, respectively). After gavage of saline pre-injected rats with tritiated glucose, plasma tritium increased rapidly (t ½ of about 8 minutes) to an asymptote that slowly declined. Subcutaneous injection with amylin dose-dependently slowed and/or delayed the absorption of the label. Plasma tritium activity was integrated over 30 minutes to obtain the areas under the curve plotted as a function of amylin dose. The $ED_{50}$ derived from the logistic fit was 0.35 µg of amylin.

We claim:

1. A method of treating or preventing pain in a mammalian subject in need thereof comprising administering to said subject an effective analgesic amount of an amylin or an amylin agonist, wherein said amylin agonist is not a calcitonin.

2. A method according to claim 1 wherein said amylin agonist is an amylin agonist analogue.

3. A method according to claim 2 wherein said amylin agonist analogue is $^{25,28,29}$Pro-h-amylin.

4. A method according to claim 1 further comprising administering to said subject a narcotic analgesic.

5. A method according to claim 2 further comprising administering to said subject a narcotic analgesic.

6. A method according to claim 3 further comprising administering to said subject a narcotic analgesic.

7. A method according to any of claims 4–6 wherein said narcotic analgesic is selected from the group consisting of morphine, pentazocine, hydromorphone, oxymorphone, levorphanol, methadone, meperidine, anileridine, alphaprodine, fentanol, codeine, oxycodone and hydrocodone.

8. A method according to claim 7 wherein said narcotic analgesic is morphine.

9. A method according to claim 7 wherein said narcotic analgesic is pentazocine.

10. A method of enhancing the analgesic activity of a narcotic analgesic comprising administering an amylin or an amylin agonist along with said narcotic analgesic, wherein said amylin agonist is not a calcitonin.

11. A method according to claim 10 wherein said amylin agonist is an amylin agonist analogue.

12. A method according to claim 11 wherein said amylin agonist analogue is $^{25,28,29}$Pro-h-amylin.

13. A method according to claim 10 wherein said narcotic analgesic is selected from the group consisting of morphine, pentazocine, hydromorphone, oxymorphone, levorphanol, methadone, meperidine, anileridine, alphaprodine, fentanol, codeine, oxycodone and hydrocodone.

14. A method according to claim 13 wherein said narcotic analgesic is morphine.

15. A method according to claim 13 wherein said narcotic analgesic is pentazocine.

16. A pharmaceutical composition comprising: (1) an amylin or a amylin agonist; and (2) a narcotic analgesic, or pharmaceutically acceptable salts thereof, wherein said amylin agonist is not a calcitonin.

17. A composition according to claim 16 further comprising a pharmaceutically acceptable carrier.

18. A composition according to claim 16 or 17 wherein said amylin agonist is an amylin agonist analogue.

19. A composition according to claim 18 wherein said amylin agonist analogue is $^{25,28,299}$Pro-h-amylin.

20. A composition according to claim 16 or 17 wherein said narcotic analgesic is morphine.

21. A composition according to claim 16 or 17 wherein said narcotic analgesic is pentazocine.

22. A method of treating or preventing pain in a mammalian subject in need thereof comprising administering to said subject an effective analgesic amount of an amylin or an amylin agonist, along with another pain relief agent, wherein said amylin agonist is not a calcitonin.

* * * * *